United States Patent
Funaro et al.

(10) Patent No.: US 9,721,066 B1
(45) Date of Patent: Aug. 1, 2017

(54) SMART FITNESS TRACKER

(71) Applicant: Centene Corporation, St. Louis, MO (US)

(72) Inventors: Jennifer Ann Funaro, Cheshire, CT (US); John Phillip Adams, Dallas, TX (US)

(73) Assignee: Centene Corporation, St. Louis, MO (US)

( * ) Notice: Subject to any disclaimer, the term of this patent is extended or adjusted under 35 U.S.C. 154(b) by 0 days.

(21) Appl. No.: 15/142,130

(22) Filed: Apr. 29, 2016

(51) Int. Cl.
*G06F 19/00* (2011.01)

(52) U.S. Cl.
CPC ...... *G06F 19/3431* (2013.01); *G06F 19/3487* (2013.01)

(58) Field of Classification Search
CPC ..... G06C 50/22; G06C 50/24; G06F 19/3431; G06F 19/3487
USPC ....................................................... 705/2–3
See application file for complete search history.

(56) References Cited

U.S. PATENT DOCUMENTS

| | | |
|---|---|---|
| 8,855,757 B2 | 10/2014 | Kapoor |
| 2008/0015422 A1 | 1/2008 | Wessel |
| 2010/0219973 A1* | 9/2010 | Griffin .................. G08G 1/005 340/944 |
| 2012/0041277 A1* | 2/2012 | Ebadollahi ........... A61B 5/0205 600/301 |
| 2012/0259657 A1 | 10/2012 | Keynan et al. |
| 2014/0125493 A1* | 5/2014 | Utter, II ............. G06F 19/3481 340/870.02 |

OTHER PUBLICATIONS

"Fitbit," Wikipedia, last modified May 29, 2016, https://en.wikipedia.org/wiki/Fitbit, 9 pages.

* cited by examiner

*Primary Examiner* — Eliza Lam
(74) *Attorney, Agent, or Firm* — Fish & Richardson P.C.

(57) ABSTRACT

Methods, systems, and apparatus, including computer programs encoded on computer storage media, for monitoring a user's health data. A wearable fitness tracking device may include a heart-rate sensor, a steps taken sensor, a display, and perform operations including: receiving, from the heart-rate sensor, data representing the user's heart rate during a time period, receiving, from the steps taken sensor, data representing the number of steps taken by the user during the time period, determining a risk score for the user using the data representing the user's heart rate during the time period and the data representing the number of steps taken by the user during the time period, comparing the risk score to a threshold risk score, determining a risk profile using a result of comparing the risk score to the threshold risk score, and presenting data for the risk profile on the display.

21 Claims, 7 Drawing Sheets

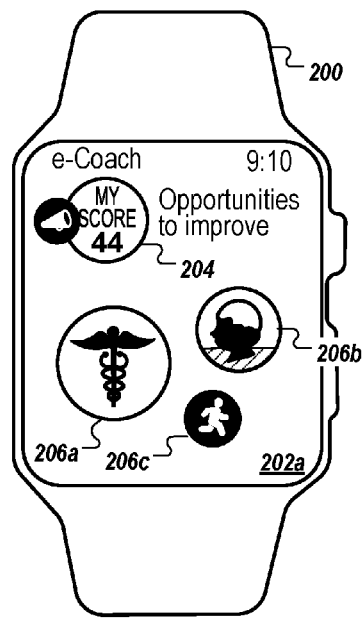
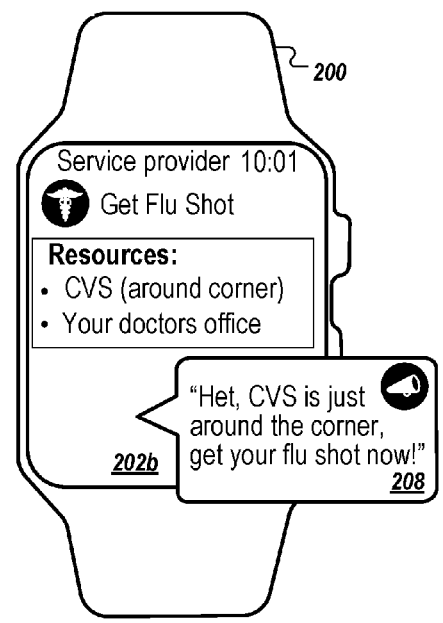
FIG. 2A
FIG. 2B
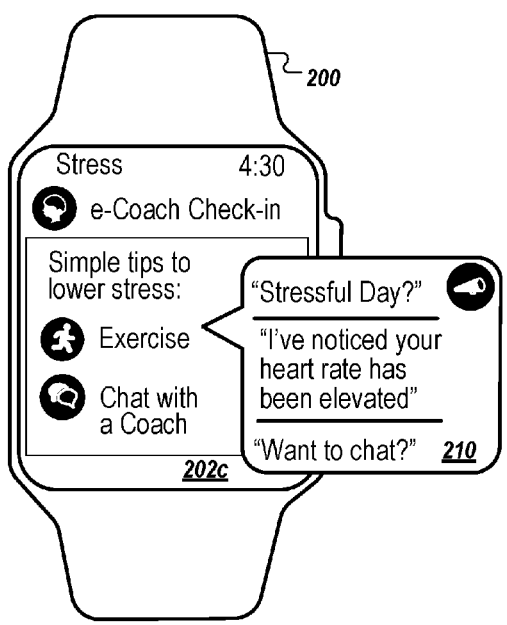
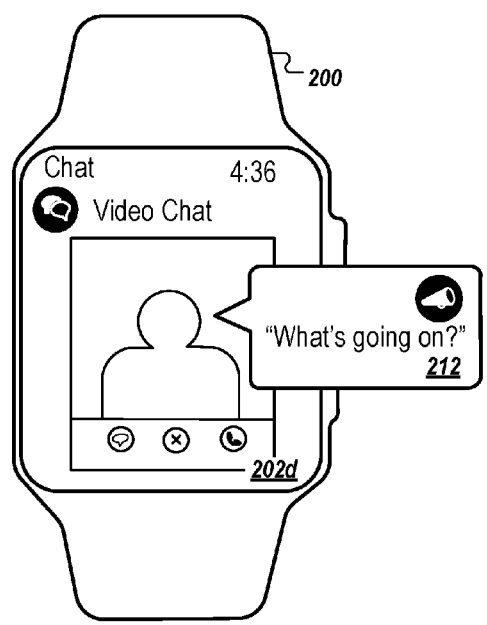
FIG. 2C
FIG. 2D

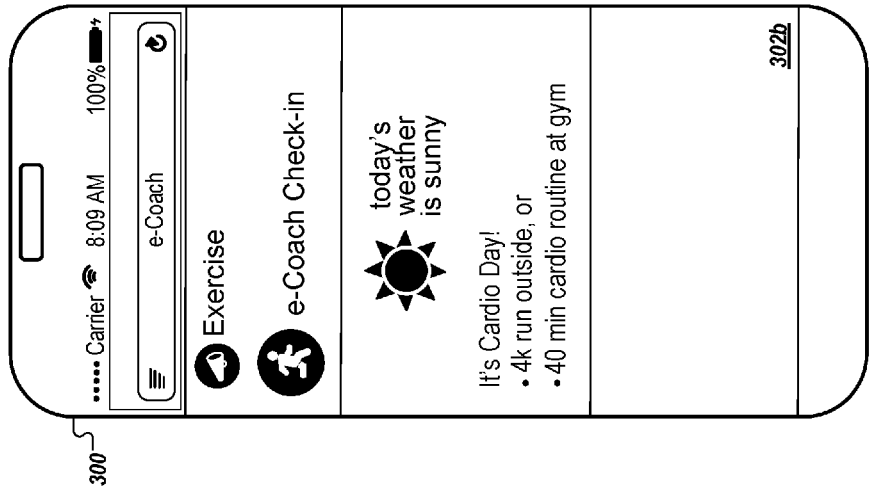
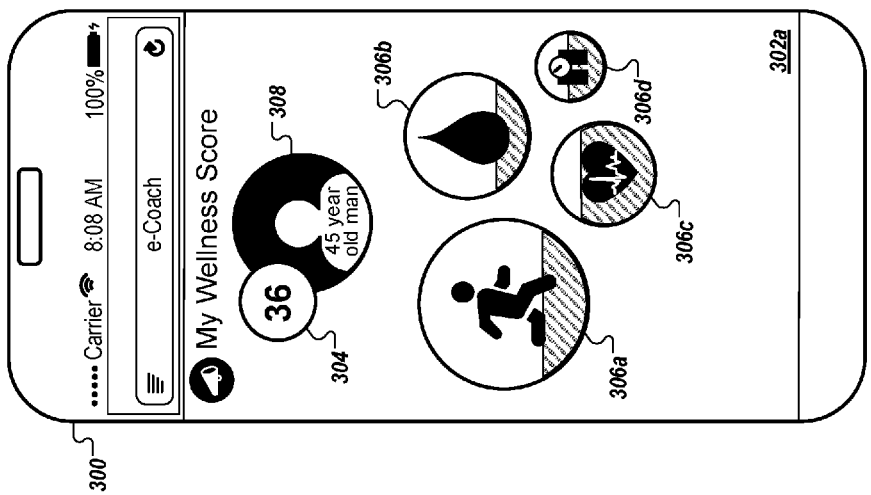
FIG. 3B
FIG. 3A

SMART FITNESS TRACKER

BACKGROUND

Some wearable devices, such as a Fitbit® or a Microsoft® Band, can measure a user's attributes, such as the user's heart rate, number of steps taken, and speed at which the user is moving, e.g., if the user is running or walking. The wearable device may present information about the user's attributes on a display.

SUMMARY

In general, one innovative aspect of the subject matter described in this specification can be embodied in methods that include the actions of receiving, from a heart-rate sensor included in a wearable fitness tracking device, data representing the user's heart rate during a time period, receiving, from a steps taken sensor included in the wearable fitness tracking device, data representing the number of steps taken by the user during the time period, determining a risk score for the user using the data representing the user's heart rate during the time period and the data representing the number of steps taken by the user during the time period, comparing the risk score to a threshold risk score, determining a risk profile using a result of comparing the risk score to the threshold risk score, and presenting data for the risk profile on a display included in the wearable fitness tracking device. Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In general, one innovative aspect of the subject matter described in this specification can be embodied in methods that include the actions of providing instructions for presentation of a suggestion that describes how a user can improve a measure of a health attribute, receiving, from a sensor that monitors a user health attribute, health data for the user, determining, using the health data, a score for the health attribute, wherein the score indicates a degree to which user performance of a task associated with the health attribute will improve the score, determining, using the score for the health attribute and historical health data for the user, whether the score for the health attribute has changed since providing the instructions for presentation of the suggestion that describes how the user can improve a measure of the health attribute, and providing instructions for presentation of data representing the score and whether the score has changed. Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination. A wearable device may include a graphics processing unit. Presenting the data for the risk profile on the display may include providing instructions for presentation of the data for the risk profile to the graphics processing unit. The graphics processing unit may cause the presentation of the data for the risk profile on the display in response to receipt of the instructions for presentation of the data for the risk profile from the data processing apparatus. The method may include, prior to receiving the data representing the user's heart rate during the time period and the data representing the number of steps taken by the user during the time period, determining a first risk score for the user using attribute data for the user, and determining that the risk score is greater than the first risk score, and presenting, on the display, score data that indicates that the risk score is greater than the first risk score in response to determining that the risk score is greater than the first risk score. The method may include receiving, from the heart-rate sensor and the steps taken sensor, some of data for the user.

In some implementations, the method may include providing data that indicates instructions for presentation of information about two or more health attributes each of which the user can improve, receiving user input that specifies selection of a particular health attribute from the two or more health attributes. Providing the data that indicates the instructions for presentation of the suggestion that describes how the user can improve a measure of a health attribute may include providing data that indicates instructions for presentation of a suggestion that describes how the user can improve a measure of the particular health attribute in response to receiving the user input that indicates the selection of one of the two or more health attributes. At least one of the sensors may monitors a measure of the health attribute of the user, may provide data representing the measure of the health attribute to the data processing apparatus, or both. Receiving, from the at least one of the sensors, the health data for the user may include receiving, from the at least one of the sensors, the measure of the health attribute of the user. The method may include determining that the measure of the health attribute of the user does not correspond to historical patterns for the health attribute. Providing the instructions for presentation of the suggestion that describes how the user can improve the measure of a health attribute may be responsive to determining that the measure of the health attribute of the user does not correspond to the historical patterns for the health attribute.

In some implementations, the method may include determining, for each of two or more health attributes including the health attribute, a second score that indicates a degree to which user performance of a task associated with the corresponding health attribute will improve the second score, and selecting, from the two or more health attributes, the health attribute with a highest second score from the second scores or a lowest second score from the second scores. Providing the instructions for presentation of the suggestion that describes how the user can improve a measure of the health attribute may include providing the instructions for presentation of the suggestion that describes how the user can improve a measure of the selected health attribute with the highest second score from the second scores or the lowest second score from the second scores. Determining, using the health data, the score for the health attribute may include determining the score for the health attribute using the health data for the user and a term in an equation used to determine an overall wellness score for the user, wherein the score indicates a degree to which user performance of a task associated with the health attribute will improve the overall wellness score. The overall wellness score may indicate a degree to which user performance of a task associated with one of two or more health attributes will improve the overall wellness score. The at least one of the two or more health attributes may include the health attribute. The method may include retrieving data representing the equation from a memory. A training system may generate at least part of the equation by fitting a model represented by the equation to historical health data for other users. The equation may include one term for each of the two or more health attributes. Determining, using the health data, the score for the health attribute may include determining, using a term for the health attribute and the health data, the score for the health attribute. A system may generate at least part of the equation using empirical data.

In some implementations, providing the instructions for presentation of the suggestion that describes how the user can improve a measure of a health attribute may include providing instructions for visual presentation of the suggestion that describes how the user can improve a measure of a health attribute. The method may include determining a physical location of the wearable device, and determining, using the physical location of the wearable device, the suggestion that describes how the user can improve a measure of a health attribute. The method may include determining a predicted future physical location of the wearable device using calendar data for the user, and determining, using the predicted future physical location of the wearable device, the suggestion that describes how the user can improve a measure of a health attribute. The method may include determining current weather conditions or predicted weather conditions for a physical area at which the wearable device will be located, and determining, using the current weather conditions or the predicted weather conditions, the suggestion that describes how the user can improve a measure of a health attribute. The method may include determining a likelihood that a physical location of the wearable device is near a physical location with at least a threshold amount of vehicle traffic, determining whether the likelihood satisfies a threshold likelihood, determining whether audio content is being presented to the user, and lowering a volume of the audio content in response to (i) determining that the likelihood satisfies the threshold likelihood and (ii) determining that audio content is being presented to the user. Receiving, from at least one of the sensors, the health data for the user may occur after providing the instructions for presentation of the suggestion that describes how the user can improve a measure of the health attribute.

The subject matter described in this specification can be implemented in particular embodiments and may result in one or more of the following advantages. In some implementations, the systems and methods described below may determine risk scores specific to a user's attributes, e.g., weight, cholesterol, lipoprotein levels, body mass index (BMI), age, sex, blood pressure, etc. In some implementations, the systems and methods described below may determine a component of a risk score that is specific to a particular attribute, may identify ways in which a user may improve the particular attribute, provide a recommendation of how to improve the particular attribute, dynamically monitor the particular attribute, e.g., using a sensor specific to the particular attribute, monitor changes to the particular attribute for the user, or a combination of two or more of these. For example, continuous monitoring of user attributes, periodic updating of a risk score for the user, and/or generation of a risk score using continuous data may provide more accurate analysis of actual risk for the user than other systems. In some implementations, the systems and methods described below may generate risk scores that account for sex-age interactions to generate recommendations that are more relevant, appropriate, or both, compared to other systems that do not account for sex-age interactions. In some implementations, the systems and methods described below may use risk scores to determine individual health goals for a user to improve their health, maintain their current health status, or both. In some implementations, the systems and methods described below may generate and provide recommendations that are specific to a user's preferences, risk score, or both. In some implementations, the systems and methods described below may continuously or substantially continuously monitor and attribute data to actively recommend tasks for a user based on the attribute data, e.g., with little to no user input used to generate the task recommendations, to provide recommendations specific to a user, or both. For instance, the systems and methods described below may generate task recommendations based on analysis of the attribute data without requiring user input requesting a task recommendation, without user input defining particular attribute data, or both.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 2A-D show another example of a wearable device that measures user attributes.

FIGS. 3A-B show an example of a mobile device that presents user interfaces with information about user attributes.

Like reference numbers and designations in the various drawings indicate like elements.

DETAILED DESCRIPTION

Figure 1C:
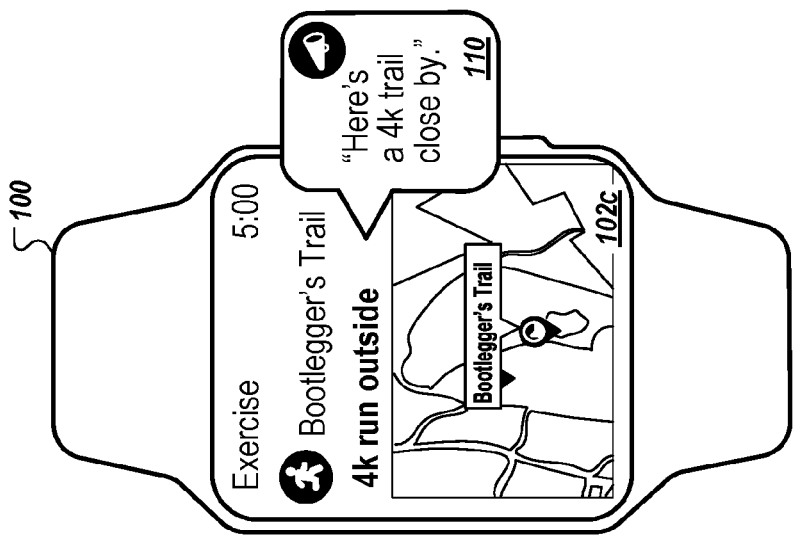
FIGS. 1A-F show an example of a wearable device that measures user attributes.

A wearable device monitors a user's attributes, such as heart rate, blood pressure, body mass index, distance walked, e.g., horizontally, vertically, or both, cholesterol, and lipoprotein levels. The wearable device includes multiple sensors, for instance one sensor for each of the attributes. In some examples, a particular sensor may generate data for multiple attributes.

The wearable device uses the attribute data to generate a score for the user, e.g., a risk score. For instance, the wearable device may select a particular predictive model from multiple predictive models depending on the particular attributes for which the wearable device has data. The wearable device uses the particular predictive model to determine an overall score for the user and may determine scores specific to each of the attributes for which the wearable device has data. An overall score indicates whether user performance of a task will improve the user's score. For instance, the overall score may indicate a degree to which user performance of a task will cause a determination of an improvement to the overall score. A score for a particular attribute indicates whether user performance of a task for the attribute will improve the attribute score and the overall score. In some examples, a lower score indicates that user performance of a task for an attribute will have a bigger impact on improving the score, e.g., the attribute score, the overall score, or both, than user performance of a task with a higher score, whether the score is specific to a particular attribute or is an overall score. In some examples, a higher score indicates that user performance of a task for an attribute will have a bigger impact on improving the score, e.g., the attribute score, the overall score, or both, than user performance of a task with a lower score.

The wearable device may use the overall score or a score for a particular attribute, e.g., heart rate, to determine a risk profile for the user. For instance, the wearable device may determine whether a score does not satisfy a threshold score, e.g., is less than a threshold score, and that the user can improve an attribute. The wearable device may compare the overall score with a threshold overall score, or a score for the particular attribute, e.g., heart rate, with a threshold attribute score.

The wearable device provides the user with feedback that identifies the score. The feedback may indicate whether the score satisfies the threshold score. For example, the wearable device may indicate that the user's blood pressure is below average, e.g., for their age and sex, and that the user should exercise more.

The wearable device may continuously monitor the user's attributes and provide feedback regarding changes to the attributes. For instance, the wearable device may determine that the user is jogging using data from the accelerometer. When the wearable device determines that the user is no longer jogging, the wearable device may determine whether one or more of the attributes has changed by a threshold amount, e.g., in response to the determination that the user is no longer jogging. Each of the attributes may have different thresholds. If the wearable device determines that the user's heart rate has changed by at least the threshold amount, e.g., has improved, the wearable device may provide feedback that indicates the improved heart rate, the change to the heart rate, or both.

In some examples, the wearable device may monitor the attributes over a period of time and determine whether an attribute continues to change, e.g., the heart rate continues to improve, reverts back to a previous value, e.g., the heart rate change was temporary, or remains at or around the new value. The wearable device may receive data for the attributes across the period of time and provide feedback after the period of time instead of immediately upon determining that the attribute has changed. For instance, the wearable device may determine that the user's heart rate improved on Monday and that the improved heart rate stays the same until Saturday. On Saturday, the wearable device may provide feedback indicating the improved heart rate.

The wearable device may use additional data when determining the overall score for the user. In some examples, the wearable device uses biometric data, health screening data, and emotional health data as the attribute data. The wearable device may use only data for modifiable attributes to determine an overall score, e.g., and not a particular disease which the user may have or family health history data. In some examples, the wearable device uses any relevant data to determine an overall score for the user, e.g., including data for a particular disease the user has, family health history data, or both. For instance, the wearable device may receive health data or family health history data that identifies an occurrence of congestive heart failure, stoke, chronic obstructive pulmonary disease, cancer, hypertension, diabetes, heart attack, or a combination of two or more of these, for the user, the user's family, or both.

The wearable device selects a predictive model depending on the types of data for the user and accuracies for the types of data. For instance, the wearable device may use a first predictive model that accepts specific attribute data as input, e.g., a heart rate of sixty beats per minute, a second predictive model that access attribute ranges as input, e.g., a heart rate between fifty-five and seventy beats per minute, or a third predictive model that accepts attribute data and family health data as input, e.g., when the family health data is stored in a memory of the wearable device. The wearable device may have different predictive models for any appropriate combination of input data.

Figure 1B:
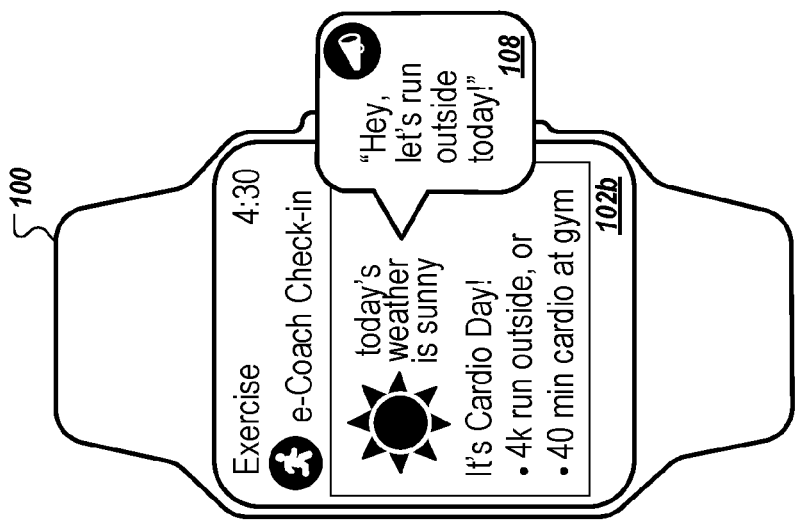
Figure 1A:
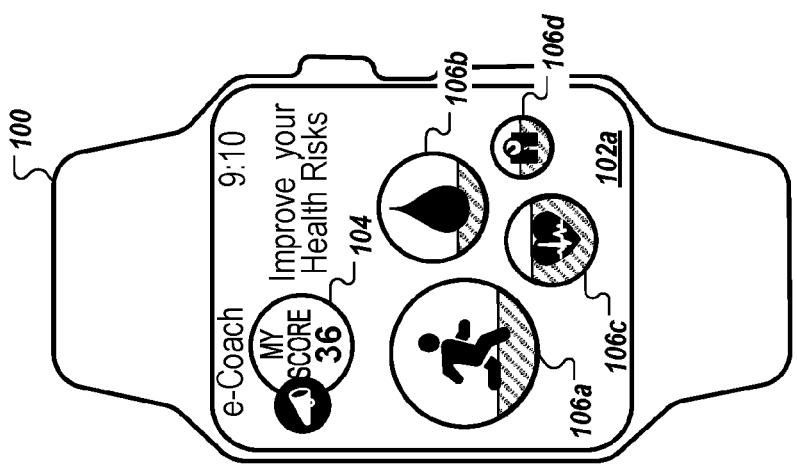

FIGS. 1A-F show an example of a wearable device 100 that measures user attributes. For instance, as shown in FIG. 1A, the wearable device 100 presents an overview user interface 102a that identifies an overall score 104 for a user. The overall score 104 represents whether a user can perform a task for one of their attributes to improve their score. For instance, when a first user has a high overall score 104 the wearable device 100 would determine that user performance of a task would have a smaller impact on changing the high overall score 104 compared to change in an overall score when a second user, with a lower overall score 104, performs the task. In some examples, the overall score 104 may indicate a risk score, a wellness score, or both.

For example, as described in more detail below, the wearable device 100 may select a predictive model based on attribute data that is stored in a memory of the wearable device 100. The predictive model may be specific to the types of attribute data in the memory, the accuracy of the attribute data, or both.

In the example shown in FIGS. 1A-F, a higher score indicates that performance of a task has a lower impact on the score. For instance, a score of fifty may indicate that the user cannot perform any task to improve their score and a score of zero may indicate that user performance of a task will have an impact on their score. In some examples, a lower score may indicate that performance of a task has a lower impact on the score. For example, a score of zero may not be impacted by user performance of a task while a score of fifty or one hundred is impacted by user performance of the task. The score may be an overall score or an attribute score for a particular attribute.

The overview user interface 102a includes attribute icons 106a-d that identify particular attributes which the user may be able to improve, e.g., based on the scores for those attributes. Details on how attribute scores are determined are described in more detail below. A first attribute icon 106a may indicate that an attribute score for exercise can be improved. A second attribute icon 106b may indicate that an attribute score for the user's lipoprotein levels can be improved. A third attribute icon 106c may indicate that an attribute score for the user's blood pressure can be improved. A fourth attribute icon 106d may indicate that an attribute score for the user's body mass index can be improved.

In some examples, a size of the attribute icons 106a-d may represent for which attribute a corresponding task will have a greater impact on the overall score 104, e.g., the size may reflect a ranking of the attribute scores. For example, the first attribute icon 106a is larger than the other attribute icons 106b-d which indicates that user performance of an exercise task will have a greater impact on their overall score compared to user performance of a task to improve their lipoprotein levels, blood pressure, or body mass index.

Each of the attribute icons 106a-d includes a fill amount that represents a quantity of tasks performed to improve the attribute. For instance, the fill amount increases as the user participates in tasks for the corresponding attribute during a particular period of time. The wearable device 100 may increase a fill amount for the first attribute icon 106a as the user exercises during the week to indicate an amount for which the user has worked on the attribute. For example, the wearable device 100 may determine that the user has exercised enough for a particular week and completely fill the first attribute icon 106a but that the user has not sufficiently worked on improving their lipoprotein levels for the week, by eating healthier. At the end of the week the wearable device 100 may determine that, although the user exercised more than they improved their lipoprotein levels, an attribute score for exercise is still less than an attribute score for lipoprotein levels, and maintain the ranking of the two attributes, exercise and lipoprotein levels, for the first attribute icon 106a and the second attribute icon 106b, respectively.

When the wearable device 100 determines that two attribute scores are the same, the wearable device 100 may select one of the attribute scores as a higher ranked attribute, e.g., for an attribute icon with a larger size, using a relationship between the corresponding attribute and other attributes that also have scores for which user performance of a corresponding task will have a larger impact on the score than tasks for other attributes, using a predetermined list that identifies the attributes, or using any other appropriate method. For instance, when the wearable device 100 determines that the attribute scores for exercise and lipoprotein levels are the same and that the attribute score for blood pressure is also in the top four scores, the wearable device 100 may select the attribute score for exercise and assign the first attribute icon 106a to exercise. In some examples, the wearable device 100 may receive input indicating a ranking of the attributes as defined by the user, an administrator, or another person.

The wearable device 100 selects an attribute and provides a recommendation user interface 102b, shown in FIG. 1B. The wearable device 100 may select the attribute in response to user input selecting the attribute, e.g., in the overview user interface 102a, in response to determining that the attribute user performance of a task for the score is likely to have a greater impact on the overall score 104 than user performance of a task for another score, in response to determining that the wearable device is at a physical location near another physical location at which a task may be performed to improve an attribute, or using any other appropriate method. In some examples, the wearable device 100 may provide a recommendation at a particular time of day, e.g., when the user is going home, based on input from the user, analysis of when the user typically performs activities that can improve their attributes, or using any other appropriate method.

In some implementations, the wearable device 100 looks at combinations of attributes, and corresponding scores, when determining a ranking of attribute scores, a combination of attributes for which to provide a recommendation, or both. For instance, the wearable device 100 determines how attributes affect each other, e.g., using a predictive model or any other appropriate method, to determine a relationship between different attributes and how the attributes affect each other. The wearable device 100 may determine that improvement of a user's scores for exercise, blood pressure, and body mass index will have a bigger impact on the overall score 104 than improvement of a score for lipoprotein levels even though the score for lipoprotein levels has the most room for improvement, e.g., the lipoprotein levels score is much lower than any of the exercise score, the blood pressure score, and the body mass index score. In this example, the wearable device 100 provides a recommendation user interface 102b for a task that will improve the user's scores for exercise, blood pressure, and body mass index.

The recommendation user interface 102b may identify one or more of the attributes to which the corresponding task applies. For instance, the recommendation user interface 102b may identify exercise when an exercise score has the most room for improvement, e.g., is lower than the blood pressure score and the body mass index score.

When the attribute is exercise, or another appropriate attribute, the wearable device 100 may determine a physical location of the wearable device 100, current or predicted weather for the physical location, or both, and use the determined information to provide a recommendation. In some examples, the wearable device 100 may determine a predicted location for the wearable device 100, e.g., using location information for a particular calendar appointment in the user's calendar, location information for where the user lives, or other appropriate data.

The recommendation user interface 102b includes information about the weather, such as an indication that it will be sunny that day, and a task recommendation for how the user can improve their exercise. The recommendation user interface 102b may provide a list of recommendations indicating that the user may run a 4 k outside or perform a forty minute cardio workout at the gym. For instance, the wearable device 100 may select the task recommendations in response to determining that the user will be at home at 5 pm, that there is a trail close to the user's home, and that the user often goes to the gym two blocks from their home.

The wearable device 100 may provide an audible recommendation 108 in addition to or instead of the visual recommendation presented in the recommendation user interface 102b. For example, the wearable device 100 may generate the audible recommendation 108 prompting the user to "run outside today," and may indicate the predicted weather for the day.

In response to user input indicating a request for a suggested location at which to run, the wearable device 100 presents a map user interface 102c that identifies "Bootlegger's Trail," shown in FIG. 3. The user input may be a voice command, a touch command, or any other appropriate type of input for the wearable device 100, e.g., input from another device. The wearable device 100 may select the suggested location using the physical location information, the predicted physical location information, a target length of exercise, either time or distance, previous locations at which the user exercised, or a combination of two or more of these.

The wearable device 100 may present an audible prompt 110 indicating the suggested location, e.g., that states "here's a 4 k trail close by." In some examples, the audible prompt 110 specifies the suggested location by prompting the user "do you want to run on Bootlegger's Trail?"

The wearable device 100 receives user input indicating acceptance of the suggested location at which to exercise and may provide instructions for going to the suggested location. The wearable device 100 may provide instructions that indicate a route for the suggested location, e.g., how the user can navigate Bootlegger's Trail. The wearable device 100 may use data from a global positioning system (GPS) included in the wearable device 100 or another device, e.g., a smart phone, to determine the instructions that indicate the route for the suggested location.

In some implementations, when the wearable device 100 determines that the user is listening to audio content, e.g., music or a radio show, the wearable device 100 may monitor for traffic, an upcoming road, or other conditions in which the audio content should be silenced, e.g., muted or paused. For instance, the wearable device 100 may determine, using information about the route for the suggested location and a current physical location of the wearable device 100, that the wearable device 100 is approaching a road and that the route will cross over the road. When the wearable device 100 determines that the wearable device 100 is within a predetermined physical distance from the road, the wearable device 100 may silence the audio content. For instance, when the wearable device 100 communicates with a smart phone, e.g., via Bluetooth, the wearable device 100 may provide commands to the smart phone to mute or pause the audio content. When the wearable device 100 provides the audio content, the wearable device 100 pauses or mutes the audio content.

Figure 1F:
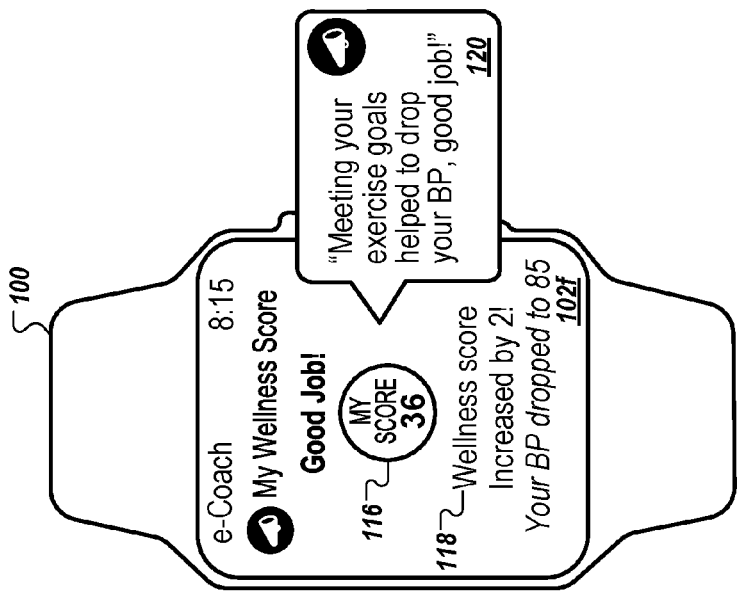
Figure 1E:
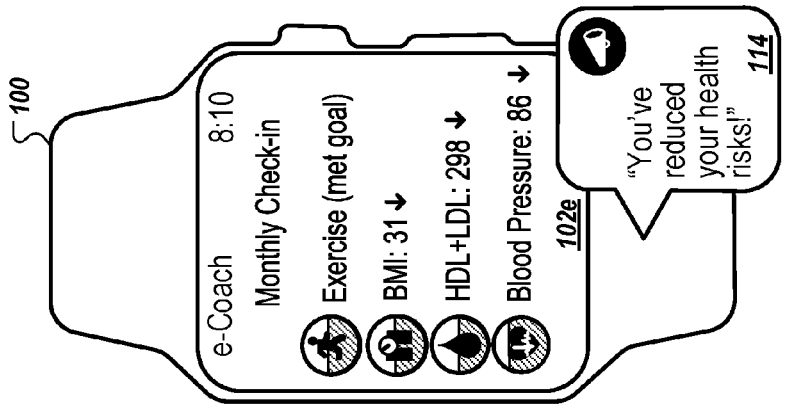
Figure 1D:
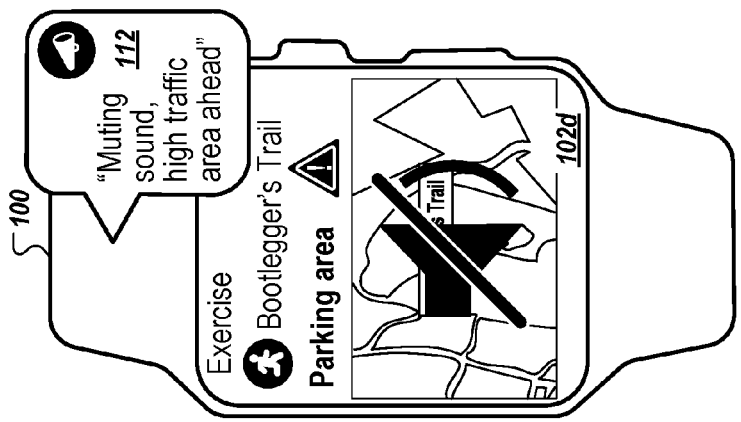

The wearable device 100 may provide a visual indication that the audio content is paused or muted, such as the audio muted user interface 102d, shown in FIG. 1D. In some examples, the wearable device 100 may indicate why the audio content is paused or muted, e.g., silenced. For instance, the wearable device 100 may provide a visual or audible alert 112 indicating that the wearable device 100, and the user, is approaching the road or a high traffic area.

The wearable device 100 may monitor traffic conditions and silence audio content upon identifying particular traffic conditions. For example, the wearable device may determine that there is an accident or high traffic on a road by route and silence the audio content. The wearable device 100 may provide an audible alert 112 that indicates the presence of the accident or the high traffic, e.g., compared to an average amount of traffic for the road. The wearable device 100 may communicate with one or more other systems, e.g., a server, to determine a volume of traffic, whether the determined volume is greater than an average amount, or to determine whether there is an accident on the route for the suggested location, or another route on or near which the wearable device 100 is travelling.

The wearable device 100 may present a status update user interface 102e, shown in FIG. 1E, that includes information about the user's attributes. For instance, the status update user interface 102e may identify particular attributes that have improved during a particular time period. In FIG. 1E, the status update user interface 102e indicates that a user's monthly exercise goal was met, body mass index went down, lipoprotein levels went down, e.g., both high-density lipoprotein (HDL) and low-density lipoprotein (LDL), and blood pressure went down.

The status update user interface 102e may indicate the time period for which the status update applies. For instance, the wearable device 100 may provide a monthly status update to a user. In some examples, the wearable device 100 may provide weekly, bi-weekly, or daily status updates to the user. For example, the wearable device 100 may present the status update user interface 102e upon detecting that a user has completed a workout. The wearable device 100 may determine the scores for the status update based on an average initial attribute data and average ending attribute data, attribute data for a specific initial and ending instance, or other appropriate attribute data.

The wearable device 100 may provide an audible update 114 that identifies the attributes which improved, how much the attributes improved, other relevant status information, or a combination of two or more of these. For instance, the audible update 114 may indicate that "you've reduced your health risks."

In some examples, a status update, whether visual, e.g., the status update user interface 102e, or audible, e.g., the audible update 114, may indicate status information for the primary attributes identified in the overview user interface 102a. In some implementations, a status update, whether visual or audible, may indicate status information for attributes that improved the most, deteriorated the most, or both. The attributes identified in the status update may be specified by the user, an administrator, or using any other appropriate method.

FIG. 1F shows an example of a score improvement user interface 102f. The wearable device 100 may present the score improvement user interface 102f in response to determining that the user completed a task to improve an attribute, e.g., the user worked out; determining that a score for the user improved, e.g., an attribute score or the user's overall score improved; or on a periodic basis, e.g., weekly, bi-weekly, or monthly.

The score improvement user interface 102f identifies a new score 116 for the user, an amount by which the score improved 118, and information about a change in an attribute of the user. In some implementations, the score improvement user interface 102f may include more or less information.

The wearable device 100 may provide an audible score improvement notification 120 that indicates that the user improved their score. The audible score improvement notification 120 may indicate that the user improved their score by exercising and that the exercise also reduced their blood pressure.

FIGS. 2A-D show another example of a wearable device 200 that measures user attributes. For instance, an overview user interface 202a, shown in FIG. 2A, indicates an overall score 204 for a user and attribute icons 206a-c that identify particular attributes which the user may be able to improve. A first attribute icon 206a indicates that the user has not received a flu shot, as indicated by the lack of any fill in the first attribute icon 206a.

User input indicating selection of the first attribute icon 206a may cause the wearable device 200 to present a flu shot user interface 202b, shown in FIG. 2B. The flu shot user interface 202b may indicate the location of a doctor's office at which the user may get a flu shot, such as a pharmacy, the user's doctor's office, or both. In some examples, an audible prompt 208 may indicate that the user may receive a flu shot at a physical location near the physical location of the wearable device 200, e.g., a store around the corner.

In some implementations, the wearable device 200 may present the flu shot user interface 202b, the audible prompt 208, or both, in response to other data. For instance, the wearable device 200 may determine a current or predicted physical location of the wearable device, attribute scores for the user, and, based on the attribute scores, that an attribute score for a flu shot is low. The wearable device 200 may provide a prompt indicating that a store is close to the current location or the predicted location of the wearable device 200 and that the user may get a flu shot at the store.

A second attribute icon 206b, shown in the overview user interface 202a of FIG. 2A, may indicate a score for an emotional health attribute, such as stress or depression. For instance, in response to receipt of user input indicating selection of the second attribute icon 206b, the wearable device may present a stress reduction user interface 202c, shown in FIG. 2C, that indicates how the user can lower their stress, e.g., by exercising or chatting with a coach. In some examples, the wearable device 200 may determine that data received from a sensor integrated into the wearable device is indicative of a user's stress level and provide the stress reduction user interface 202c in response.

For instance, the wearable device 200 may include a spectrophotometer that measures biometric attributes of a user that is wearing the wearable device 200, such as the user's blood pressure. The wearable device 200 may determine the biometric attributes, using data received from the spectrophotometer. The wearable device 200 may determine patterns in the biometric data that indicate stress events and, in response, determine that the user's stress level is high. Upon determining that the user's stress level is high, the wearable device 200 may provide the stress reduction user interface 202c. In some examples, the wearable device 200 may present the stress reduction user interface 202c in response to determining that the user's stress level has been high for a threshold period of time, e.g., two hours, six hours, etc.

The wearable device 200 determines the threshold period of time using data for the user. For instance, the wearable device 200 continuously, substantially continuously, or periodically measures attribute data for the user to determine patterns in the user's attribute data. The wearable device 200 may determine that a first user has a high blood pressure periodically throughout a day and that high blood pressure for an extended period, e.g., six hours, is indicative of high stress for the first user. The wearable device 200 may determine for a second user that the second user rarely has high blood pressure and that a short period of high blood pressure, e.g., one hour, is indicative of high stress for the second user.

The wearable device 200 may customize the stress reduction user interface 202c using attribute scores for the user, user preferences, statistical data that indicates tasks which are likely to reduce stress, e.g., specific to other attribute data for the user, other appropriate data, or a combination of two or more of these. For instance, the wearable device 200 may determine that during the day the user typically reduces their stress by taking a five minute walk or meditating and provides a prompt that indicates one or both of these tasks as a way in which the user may reduce their stress.

The wearable device 200 may provide an audible notification 210 prompting the user to indicate whether they have had a stressful day. For instance, the audible notification 210 may indicate that the user's heart rate has been elevated, or that the wearable device 200 determined another attribute has levels indicative of stress. The audible notification 210 may prompt the user whether the user would like to chat with a coach.

In response to receipt of data indicating that the user would like to chat with a coach, whether audible data or touch screen input data, the wearable device 200 may present a video chat user interface 202d, shown in FIG. 2D.

The video chat user interface 202d may present a video image of a coach and provide a user with chat options, e.g., an option to create and send a text message to a coach, to initiate or end a video or audio call with the coach, and other appropriate chat options.

The wearable device 200 may present audio content 212 with the video chat user interface 202d, such as an audible conversation between the user and the coach. For example, the wearable device 200 may include a microphone to capture utterances spoken by the user for the conversation, a speaker to present the audio content 212, e.g., that includes the utterances of the coach, a display to present video images of the coach, and a camera to capture video images of the user. In some examples, the wearable device 200 may cause the presentation of the video chat user interface 202d on another device, e.g., a smart phone, or may use another device to facilitate the presentation of content for the video chat user interface 202d. For instance, the wearable device 200 may present the video chat user interface 202d on a display integrated into the wearable device 200 and may use a microphone and speaker included in another device, such as a smart phone or a headset.

A third attribute icon 206c in the overview user interface 202a, shown in FIG. 2A, indicates that the user has reached their exercise goal for a particular period of time. For instance, the complete fill of the third attribute icon 206c indicates that user performance of a task for exercise will have little to no impact on the user's overall score 204 compared to user performance of a task for a different attribute, e.g., getting a flu shot, decreasing their stress, or meeting with a coach. In some examples, the fill for a third attribute icon 206c may indicate that the user should perform tasks for other attributes so that the user is less likely to focus on improving only one attribute.

The wearable device 200 may include the third attribute icon 206c in the overview user interface 202a previously when the user has achieved an exercise goal for a particular period of time, e.g., a week. As the wearable device 200 monitors the user's attributes and determines that the user is exercising, the wearable device 200 increases the fill for the third attribute icon 206c until the wearable device 200 determines that the user attribute data indicates that the user has achieved their exercise goal for the particular period of time.

In some implementations, when the wearable device 200 determines that a score for an attribute for which an icon was presented in the overview user interface 202a indicates that user performance of a task for the attribute will have less impact on the overall score 204 than when the icon was initially presented in the overview user interface 202a, the wearable device 200 may remove the attribute icon from the overview user interface 202a, present a user interface indicating that the user has achieved a goal for the attribute, replace the icon with an icon for another attribute, e.g., for which user performance of a task will impact the overall score 204, or a combination of two or more of these.

FIGS. 3A-B show an example of a mobile device 300 that presents user interfaces 302a-b with information about user attributes. The mobile device 300 may include one or more sensors that measure attributes of a user, may receive data from one or more external sensors that measure attribute of the user, or both. The mobile device 300 may present an overview user interface 302a, shown in FIG. 3A, that includes an overall score 304 for a user and attribute icons 306a-d, as described above.

The overview user interface 302a may include attribute information 308 about the user. For instance, the attribute information 308 may indicate that the user is a forty-five year old male.

The mobile device 300 may use the attribute information 308 as input to a predictive model when generating the overall score 304. In some implementations, the mobile device 300 may use the attribute information 308 when selecting a predictive model for generation of the overall score 304. For instance, the mobile device 300 may have a first predictive model for forty-five year old males and a second predictive model for forty-five year old females, in addition to predictive models for other age and sex combinations. The mobile device 300 may store the predictive models in a memory. In some examples, the mobile device 300 may request one or more predictive models from a server.

The mobile device 300 may present a recommendation user interface 302b, shown in FIG. 3A, in response to user input selecting the first attribute icon 306a in the overview user interface 302a. The recommendation user interface 302b may include information about how the user can improve the attribute that corresponds to the first attribute icon 306a, such as the user's exercise as described in more detail above.

Figure 4:
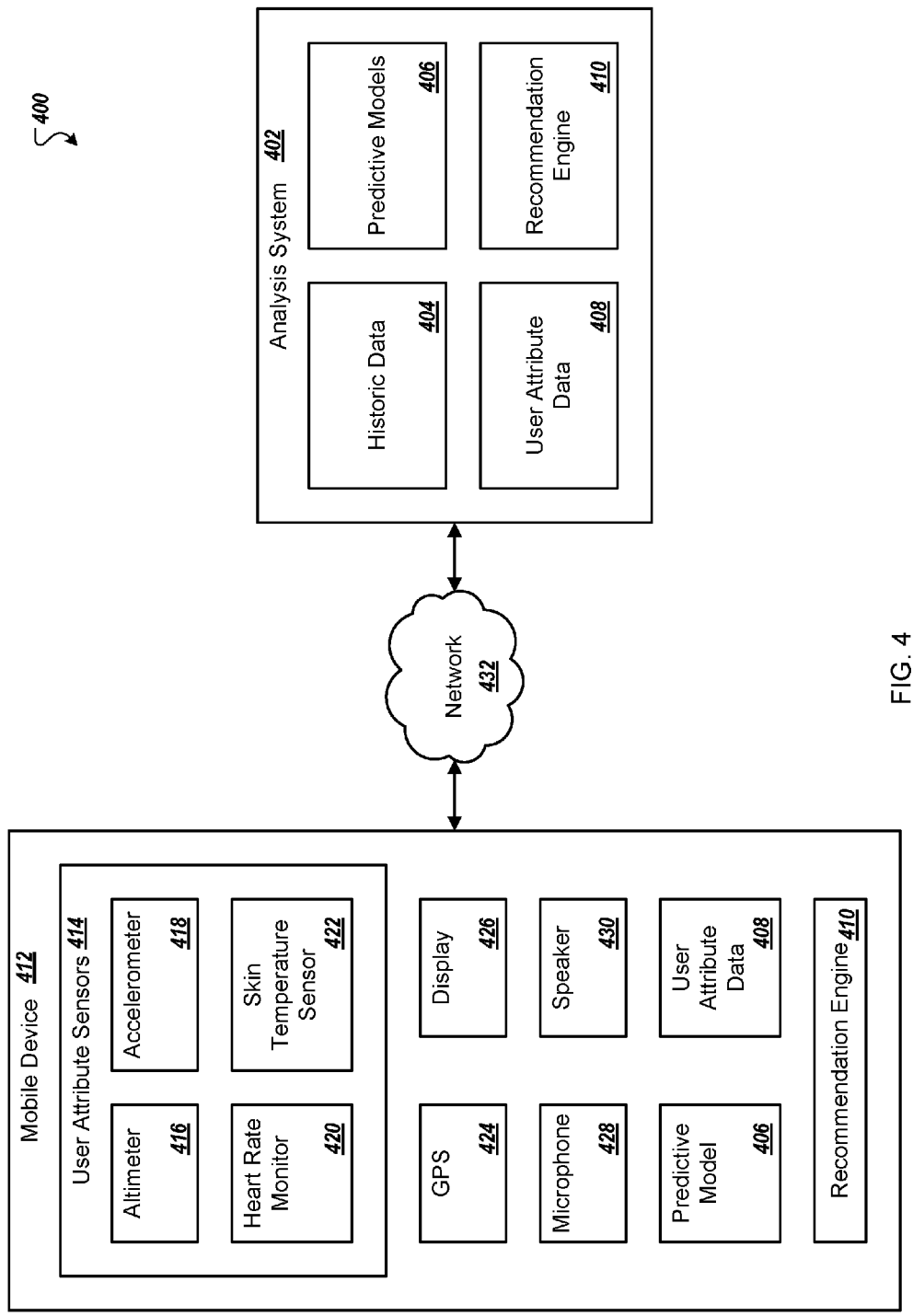
FIG. 4 is an example of an environment for determining a risk score.

FIG. 4 is an example of an environment 400 for determining a risk score. The environment 400 includes an analysis system 402 that uses historic data 404 to generate one or more predictive models 406. For instance, the historic data 404 may include health and nutritional survey result data, e.g., from the National Health and Nutrition Examination Survey. The historic data 404 may include empirical data, e.g., survey data for stress, depression, or both. In some examples, the historic data 404 may include preventive screening data, e.g., for flu shots, mammograms, cervical screenings, colonoscopies, or a combination of two or more of these. The analysis system 402 may receive the historic data 404 from multiple different sources. The analysis system 402 may store parts of the historic data 404 in different databases, e.g., each of which may correspond to a source of the data.

The analysis system 402 creates predictive models 406 that receive, as input, user attributes such as sex, age, whether the user smokes, whether and how much the user exercises, body mass index, blood pressure, total cholesterol, high-density lipoprotein (HDL) level, chronic disease diagnosis, or a combination of two or more of these. For instance, the analysis system 402 may create a first predictive model that accepts, as input, specific numeric values for HDL, total cholesterol, and blood pressure, e.g., diastolic blood pressure (DBP). The analysis system 402 may create a second predictive model that accepts, as input, numeric ranges for HDL, total cholesterol, blood pressure, or two or more of these. The second predictive model may accept specific numeric values for some input attribute values while accepting a numeric range for at least one of the attributes. The analysis system 402 may create a third predictive model that accepts input when at least one of HDL, total cholesterol, or blood pressure are unknown, e.g., and attribute values are known for the other input attributes.

In some examples, the analysis system 402 may determine a sex and age relationship, a sex and body mass index relationship, or both, and use those relationships as input to the predictive model. The analysis system 402 may use data representing the relationships during predictive model generation, run-time use of the predictive model, or both.

In some implementations, the analysis system 402 may generate different predictive models for different sex and age combinations. For instance, the analysis system 402 may generate a first predictive model for males between thirty and thirty-five, a second predictive model for females between thirty and thirty-six, and a third predictive model for males between sixty-two and sixty-five, in addition to other predictive models for different age and sex combinations.

The analysis system 402 may create different predictive models that accept different attribute input data. For instance, the analysis system 402 may create a first predictive model that accepts exercise, blood pressure, body mass index, total cholesterol, HDL, sex, and age as input, a second predictive model for stress and depression, and a third predictive model for preventive screening data. In some examples, one of the predictive models may accept data indicating a particular disease of the user, medical history data for the user, e.g., self-reported medical history data, family medical history data, or both. For instance, the analysis system 402 may receive data, e.g., family medical history data or self-reported medical history data, in response to user input in a questionnaire and use the data to determine the family medical history data, the data indicating the particular disease of the user, or both.

The analysis system 402 may combine an output of the multiple predictive models, or use output from a single predictive model, to determine an overall score for the user. For instance, the overall score is a measure of modifiable attributes and whether any of those modifiable attributes may be changed. The overall score may not reflect whether there is a likelihood that a user i) may recover from a particular disease, ii) have a condition identified in the family medical history data, or iii) both. When the analysis system 402 combines output from multiple predictive models, the analysis system 402 may combine data from predictive models that accept different types of input data, such as the first predictive model, second predictive model, and third predictive model mentioned in the previous paragraph.

The analysis system 402 may receive user attribute data 408 for a particular user and provide the user attribute data 408 to a recommendation engine 410. For example, the analysis system 402 may receive the user attribute data 408 from a mobile device 412, another computer, e.g., a desktop or a laptop, or both. The user attribute data 408 may be in the form of survey data, data measured by user attribute sensors 414 included in the mobile device 412, medical or pharmacy data, e.g., from a doctor's office, another appropriate source, or a combination of two or more of these. In some examples, the user attribute data 408 may be data from a biometric screening, a health risk assessment, a questionnaire, or two or more of these.

The user attribute data 408 may include personal data, such as a user's sex. The user attribute data 408 may include biometric data, such as a user's age, weight, height, blood pressure, total cholesterol, HDL cholesterol, or other appropriate biometric data. The user attribute data 408 may include health behavior data, such as a total number of minutes of exercise per week, an intensity level for exercise, e.g., overall or for particular exercise activities, whether and how much a user smokes, or other appropriate health behavior data. The user attribute data 408 may include emotional health data that represents a user's rating of their amount of control, e.g., lack of control, in their life for a particular period of time, e.g., the previous week, month, three months, etc.; a user's rating of their confidence ability to handle personal problems for the particular period of time; a user's rating of how often things are going their way during the particular period of time; a user's rating of how often the user felt difficulties were piling up and could not be overcome; a user's depression rating; or a combination of two or more of these. The analysis system 402 may use different periods of time for different types of attribute data. The user attribute data 408 may include current health data for the user, such as whether a female user had a pap smear in the past three years, whether the user had a flu shot in the past year, whether a female user has received a mammogram at least every two years, and/or whether a male user has received a prostate exam.

The recommendation engine 410 applies the user attribute data 408 to one of the predictive models, e.g., specific to the particular user, the user attribute data 408, or both. For instance, the recommendation engine 410 may select a particular predictive model from the predictive models 406 based on the types of user attribute data 408 for the user, e.g., specific numerical values, numerical ranges, no numerical data, whether disease or family medical history data is available, etc., or based on particular attribute data for the user, e.g., age, sex, or both. In some examples, the recommendation engine 410 may select the particular predictive model based on both the types of user attribute data 408 for the user and particular user attribute data 408 for the user.

In some implementations, the analysis system 402 represents the particular predictive model as an equation with weights. When the recommendation engine 410 applies the particular predictive model to the user attribute data 408, the recommendation engine 410 combines a value for a particular attribute, such as body mass index, with the corresponding weight to determine a weighted value for the particular attribute. The recommendation engine 410 may use the weighted value for the particular attribute as an attribute score that indicates an extent to which user performance of a task for the attribute is likely to improve the user's overall score, the attribute score, or both. The weighted value may be a decimal value, may be a value that falls within a particular range of values, or any other appropriate value. The analysis system 402 may scale the value to be within a predetermined range of permissible scores.

The recommendation engine 410 combines each of the weighted values to determine an overall score for the user. For instance, the recommendation engine 410 may add or multiply the weighted values together to determine the overall score.

In some implementations, the recommendation engine 410 uses different weights for a particular predictive model 406 depending on ranges of input values. For example, the analysis system 402 may include three predictive models, each of which accept different types of input combinations. A first predictive model may accept numeric values for high-density lipoprotein, total cholesterol, and diastolic blood pressure, in additional to numeric values for other attributes. A second predictive model may accept numeric ranges as input for at least one of high-density lipoprotein, total cholesterol, and diastolic blood pressure, in additional to numeric values for other attributes. A third predictive model may accept numeric input, whether particular values or ranges, when values for one or more of high-density lipoprotein, total cholesterol, and diastolic blood pressure are unknown.

The recommendation engine 410 may change weights in one or more of these models based on an age for a user to which input attribute data belongs. For instance, the recommendation engine 410 may, for a first user, determine that the first user is thirty and to use a first weight for users between the ages of twenty-one and thirty, inclusive. The recommendation engine 410 applies the first weight to a selected predictive model and inputs attribute data for the first user into the selected predictive model to determine an overall score for the first user. When the first user turns thirty-one, the recommendation engine 410 determines a second weight and applies the second weight to the selected predictive model to determine an overall score for the user. The recommendation engine 410 may determine different weights for a user using the user's age based on a relationship between the user's age and attributes. In some implementations, the recommendation engine 410 uses different predictive models for different age ranges when the predictive models include different weights.

In some examples, the recommendation engine 410 may include different weights for different age ranges depending on a sex of the user. For instance, the recommendation engine 410 may select a first weight for a twenty-three year old male and a second, different weight for a twenty-three year old female.

In some implementations, the analysis system 402 creates an initial predictive model using first historical data and creates one or more equations using second historical data. The analysis system 402 combines the initial predictive model and the one or more equations to create a predictive model for the predictive models 406. For instance, the analysis system 402 fits an equation to health and nutritional survey result data to generate the initial predictive model. The analysis system 402 creates one or more equations for empirical data, historic data, or both. For instance, the analysis system 402 may create a first equation for empirical data and create a second equation for historic data. The analysis system 402 combines the initial predictive model, the first equation, and the second equation to create a predictive model and stores the created predictive model in the predictive models 406, e.g., in a memory included in the analysis system 402.

In some implementations, the recommendation engine 410 may use the overall score as a risk score to determine a risk profile for the user. The risk profile may indicate particular attributes or combinations of attributes for which the user can improve. For instance, the recommendation engine 410 may determine whether the overall score satisfies a threshold score value, e.g., is greater than or equal to the threshold score value.

When the overall score satisfies the threshold value, the recommendation engine 410 may assign a low risk profile to the user. The low risk profile may indicate that the user has few, if any, attributes which they can improve. The recommendation engine 410 may use the attribute scores for the individual attributes to determine which specific attributes the user can improve.

The recommendation engine 410 may determine the risk profile, the overall score, or both, periodically or substantially continuously. In some examples, the recommendation engine 410 may determine a risk profile for a user once, e.g., when initially analyzing a user's attribute data. The recommendation engine 410 may determine a risk profile in response to receipt of user input that indicates a request for a risk profile.

When the overall score does not satisfy the threshold value, the recommendation engine 410 may determine whether the overall score belongs to a medium or high risk profile. For instance, the analysis system 402 may include multiple different score thresholds, each of which are for a different risk profile, e.g., a first medium risk profile, a second medium risk profile, and a high risk profile.

In some examples, the recommendation engine 410 may determine a profile for a particular attribute using the attribute score. For instance, the recommendation engine 410 may determine that the user's overall score places the user in a low risk profile but the user should exercise more to maintain their overall score.

The analysis system 402 may receive data determining the threshold score values by analyzing the historic data 404 or in response to user input selecting one or more threshold scores. For instance, the analysis system 402 may determine the threshold scores based on types of actions for the corresponding users to preform, e.g., for particular attributes with scores that do not satisfy a threshold score. In some examples, the analysis system 402 may receive user input from an administrator defining the threshold scores.

The recommendation engine 410 may use a combination of both a risk profile and the attribute scores to determine recommendations for the types of actions a user can perform to improve their overall score. Since the attribute scores and the overall score for a particular user are based on continuous data, the recommendation engine 410 may determine actions specific to the attributes of the user and not solely based on whether the user is high risk or low risk.

For instance, the recommendation engine 410 may determine that both a first user and a second user have a high risk for exercise, based on corresponding exercise attribute scores. The recommendation engine 410 may determine that a first exercise score for the first user is just below a threshold exercise score and that the user can go on a fifteen minute walk three times a week at a certain intensity to bring their exercise score above the threshold exercise score, e.g., in addition to any other exercise the first user already performs. The recommendation engine 410 may determine that a second exercise score for the second user is well below the threshold exercise score and that the user should perform aerobic activity for thirty minutes three times a week and go swimming for an hour twice a week, e.g., in addition to any other exercise the second user already performs. In these examples, the recommendation engine 410 uses the risk profile to determine whether a user should improve an attribute and the attribute scores, which are based on continuous data, to determine a task to perform to improve the attribute.

The analysis system 402 may generate the predictive models 406 so that the recommendation engine 410 determines, using the user attribute data 408 for various users, the users which have at least a threshold probability of developing a chronic disease and tasks for those users to reduce the likelihood that they will develop a chronic disease. For instance, the analysis system 402 may generate each of the predictive models 406 to determine likelihoods that a user will get cancer, diabetes, sleep apnea, or another chronic disease. The recommendation engine 410 uses the predictive models 406 to generate scores for each of the user attributes to reduce the likelihood that the user will get the chronic diseases. In some examples, the analysis system 402 does not determine likelihoods that a user will get a chronic disease and the recommendation engine 410 determines task recommendations that may reduce the likelihood that the user will get the chronic disease.

In some implementations, the recommendation engine 410 may determine an attribute score for a user likelihood of dying because of a particular disease, an attribute score for a user likelihood of developing a disease or a particular disease, or both. For instance, the recommendation engine 410 may use a predictive model and user attribute data to determine a score that is indicative of the user developing a particular disease. The recommendation engine 410 may use the score to determine task recommendations to improve the score, e.g., to reduce the likelihood that the user will develop the particular disease.

The analysis system 402 may generate predictive models 406 that have non-linear fits. For instance, the recommendation engine 410 may use the non-linear fits from the predictive models to determine that a user with a very low body mass index, e.g., below a first threshold, or a high body mass index, e.g., above a second threshold, can improve their overall score by changing their body mass index. For a second user with a body mass index between the first threshold and the second threshold, inclusive, the recommendation engine 410 may determine that the second user does not need to improve their body mass index. Since the recommendation engine 410 uses continuous data, the recommendation engine 410 may determine that the second user's body mass index satisfies both thresholds and is close to one of the threshold values. In this example, the recommendation engine 410 may provide a recommendation indicating a task the second user can perform to improve their body mass index, maintain their body mass index within the threshold values, or both.

In some examples, the recommendation engine 410 may use a predictive model that attenuates different user attribute data 408. For instance, the recommendation engine 410 may receive user attribute data 408 for a user with high cholesterol and high-density lipoprotein (HDL) and assign the user to a low risk profile, e.g., for cholesterol or in general.

The recommendation engine 410 may provide a user's overall score to a mobile device 412 for presentation to a user. For instance, the mobile device 412 may include one or more user attribute sensors 414, such as an altimeter 416, e.g., which measures elevation changes, an accelerometer 418, e.g., a steps taken sensor, a heart rate monitor 420, and a skin temperature sensor 422. In some examples, the user attribute sensors 414 may include one or more spectrophotometer, e.g., to measure cholesterol, metabolite levels, or other appropriate biometric attributes. The mobile device 412 receives data from one or more of the user attribute sensors 414 and provides the data to the recommendation engine 410 as the user attribute data 408.

The recommendation engine 410 uses the user attribute data 408 and a predictive model 406 to generate an overall score for the user, a risk profile for the user, or both. The risk profile may be an overall risk profile, a risk profile for a particular attribute, or indicative of both.

In some examples, the recommendation engine 410, a predictive model 406, and the user attribute data 408 are included on the mobile device. For instance, the mobile device 412 may provide the analysis system 402 with some of the user attribute data 408. The analysis system 402 determines a predictive model from the predictive models 406 that is specific to the user of the mobile device 412 and provides the predictive model to the mobile device 412. The mobile device 412 stores the received predictive model in a memory and uses the predictive model 406 with the user attribute data 408 and the recommendation engine 410, e.g., a software module, to generate an overall score for the user.

When mobile device 412 includes the recommendation engine 410, the recommendation engine 410, or another software module, may monitor overall scores, attribute scores, or both, over time to determine how the scores change throughout the day, week, month, or another appropriate period of time. The recommendation engine 410 may use the monitored score information, and data representing how the scores change over time, to determine recommendations specific to the user and whether a change in a score occurs at least a threshold frequency of time, e.g., the user's heart rate is typically at a certain level below or above an average level at a particular time of day. For instance, when a change occurs at least a threshold frequency of time, assuming that the change is not unhealthy, the mobile device 412 may take no action. When the mobile device 412 determines that a change occurred and that the change does not occur at least the threshold frequent of time, the mobile device 412 may prompt the user to perform a particular task, e.g., go on a walk or visit a doctor.

In some examples, the recommendation engine 410 may learn user preferences, such as when a user typically works out, e.g., whether an occurrence of the user working out at a particular time satisfies a threshold value, types of food the user prefers to eat, types of tasks the user prefers to perform, or any other appropriate user preference. The recommendation engine 410 may use the user preferences when making a task recommendation. For instance, the recommendation engine 410 may determine that the user typically eats lunch around 11 AM on weekdays, that it is 10:58 AM on a Friday, and that there are two healthy restaurants near the physical location of the mobile device 412, a French restaurant and a Spanish restaurant. The recommendation engine 410 uses the user preferences to determine that the user prefers Spanish food and provides a recommendation, to the user, that the user eat at the Spanish restaurant for lunch.

The mobile device 412 presents the overall score on a display 426 or using a speaker 430 to provide an audible presentation of the overall score. For instance, the mobile device 412 may present the overall score and other data related to the overall score as described in more detail above.

The mobile device 412 may include a global positioning system (GPS) 424 that monitors a physical location of the mobile device 412. The mobile device 412 may use the GPS 424 to determine recommended tasks for a user, such as a location at which to exercise, a healthy restaurant at which to get lunch, or another appropriate task.

The mobile device 412 may include a microphone 428 to receive user input, such as a selection of an attribute for the user, e.g., to improve, a particular activity for the user to perform, or other appropriate user input. In some examples, the mobile device 412 may use the microphone 428 to receive user input when presenting content via the speaker 430. When the mobile device 412 presents content on the display 426, the mobile device may receive user input from a touch screen surface included in the display 426, hard or soft buttons included in the mobile device 412, or any other appropriate input.

The mobile device 412, the analysis system 402, or both, may receive data for a user over a period of time and determine historical attribute patterns, recommendations specific to the user, or both, using the data. For instance, the mobile device 412 monitors the user's attributes to determine historical patterns, or norms, in the attribute data for the user which may not be patterns for other users. The mobile device 412 is able to use the attribute data and the historical patterns for the attribute data to customize recommendations for the user and determine when a value for a particular attribute does not align with the historical pattern for the user.

For instance, the mobile device 412 may determine historical patterns in a user's heart rate throughout a day, whether any day, a weekday, or a weekend day. The mobile device 412 monitors the user's heart rate to determine data representing the user's heart rate. The mobile device 412 compares the data representing the user's heart rate with the historical patterns for the user's heart rate to determine whether a current heart rate, or a current heart rate pattern for a current period of time, e.g., an hour, aligns with the historical patterns.

When the current heart rate and current heart rate pattern align with the historical patterns, the mobile device 412 may determine whether to prompt the user based on the value of the actual heart rate, historical data indicating actions the mobile device 412 previously performed when detecting those historical patterns, or perform another appropriate action. For instance, the mobile device 412 may determine that when the mobile device 412 prompts the user to take a five minute break, the user's heart rate has typically gone down afterward, e.g., after the user has taken a five minute break.

When the current heart rate or the current heart rate pattern do not align with the historical patterns, the mobile device 412 may prompt the user with an interface indicating the heart rate, the heart rate pattern, or both. For instance, the mobile device 412 may generate a user interface that indicates that the user's heart rate has been elevated for the past hour. The mobile device 412 may generate a user interface suggesting tasks for the user to perform to lower their heart rate, such as talking with a coach or another appropriate action.

The mobile device 412 and the analysis system 402 may collect data in response to receipt of user input indicating a user's permission to collect data. For instance, when first used, the mobile device 412 may prompt the user for permission to collect and analyze attribute data for the user. The mobile device 412 may prompt the user for permission to send attribute data to the analysis system 402 for analysis, e.g., when the mobile device 412 does not include the recommendation engine 410 and must send data to the analysis system 402 for recommendation generation. In some implementations, the mobile device 412, the analysis system 402, or both, may receive separate permission to store data for different types of attributes.

The mobile device 412 and the analysis system 402 may store user attribute data in a way in which user identifiable information is removed. For example, a user's identity may be treated so that no personally identifiable information can be determined for the user.

The mobile device 412 may include smart phones, wearable devices, e.g., s smart watch, and other mobile devices that can send and receive data over a network 432. The network 432, such as a local area network (LAN), wide area network (WAN), the Internet, or a combination thereof, connects the mobile device 412 and the analysis system 402.

In some implementations, the mobile device 412 or the analysis system 402 may provide another device with recommendation information, score information, or both. For instance, the mobile device 412 may provide a streaming media device with a user's overall score and an attribute score, e.g., for an attribute for which the user performance of a task is more likely to improve the overall score than user performance of a task for another attribute. The mobile device 412 may provide the streaming media device with instructions to cause the streaming media device to present the overall score, the attribute score, or both in a user interface. In some examples, the mobile device 412 may provide the streaming media device with data indicating a recommendation for a task to perform.

The streaming media device may present a user interface, in response to receipt of the instructions from the mobile device 412, that identifies the overall score. The streaming media device may allow user input that indicates a request for presentation of an attribute score, a task recommendation, or both. In response to receipt of the user input, the streaming media device generates instructions for presentation of a user interface that includes the requested data. The streaming media device may provide the instructions to a television or a monitor to cause the television or monitor to display the user interface.

Figure 5:
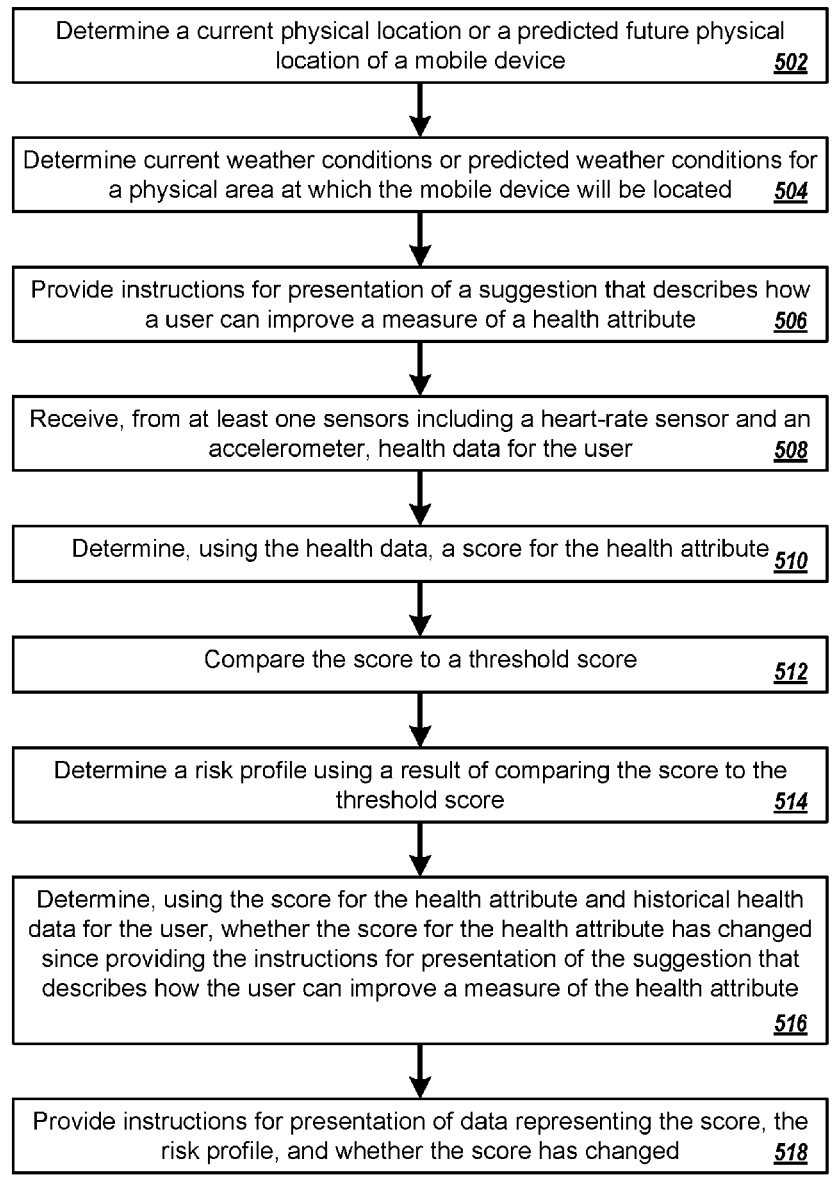
FIG. 5 is a flow diagram of a process for generating a risk score.

FIG. 5 is a flow diagram of a process 500 for generating a risk score. For example, the process 500 can be used by the mobile device 412 from the environment 400.

A mobile device determines a current physical location or a predicted future physical location of the mobile device (502). For instance, a wearable device may use calendar information for a user of the wearable device or predicted schedule information to determine the predicted future physical location. The predicted schedule information may be based on historical location data for the wearable device. For example, the wearable device may determine that on non-holiday weekdays, the wearable device is typically at an office location from 9 AM to 5 PM, at a gym location from 5:30 PM to 7 PM, and at a home location after 7:30 PM.

The mobile device determines current weather conditions or predicted weather conditions for a physical area at which the mobile device will be located (504). For instance, the wearable device may receive the weather information from a server, e.g., that stores the weather information. The weather conditions may be for the current physical location or the predicted future physical location.

The mobile device provides instructions for presentation of a suggestion that describes how a user can improve a measure of a health attribute (506). For instance, a recommendation engine included in the wearable device may use the location information, the weather information, and user attribute scores to determine the suggestion for a task the user may perform to improve one of the user's attributes. The recommendation engine may generate the user attribute scores, and an overall score, using initial data for the user, e.g., from a biometric screening, questionnaire data, sensors included in the wearable device, another appropriate data source, or a combination of two or more of these.

The mobile device receives, from at least one sensors including a heart-rate sensor and an accelerometer, health data for the user (508). The wearable device may determine that the user is performing the task determined by the recommendation engine. The wearable device may monitor the user's attributes while the user performs the task, periodically, or continuously, e.g., while the wearable device is worn by the user. In some examples, the mobile device may monitor some user attributes continuous, e.g., heart rate and steps taken, and monitor other user attributes periodically, e.g., body mass index and total cholesterol.

The mobile device determines, using the health data, a score for the health attribute (510). For instance, the wearable device may determine an updated score, e.g., risk score, for the health attribute or an updated overall score using the health data for the user received during step 508.

In some examples, the mobile device may determine a score using attribute data received during step 508 and other attribute data. For instance, the mobile device may use the user's age, sex, questionnaire data, and data received from the sensors to determine the score for the health attribute.

The mobile device compares the score to a threshold score (512). For instance, the wearable device determines whether the score satisfies the threshold score, e.g., whether the score is greater than or equal to the threshold score.

The mobile device determines a risk profile using a result of comparing the score to the threshold score (514). For example, the wearable device selects a low risk profile when the score satisfies the threshold score. The wearable device may select a medium or high risk profile when the score does not satisfy the threshold score. The medium or high risk profile may indicate that the user can improve the health attribute.

In some implementations, the mobile device may determine an overall score, e.g., during step 510. The mobile device compares the overall score to a threshold overall score, e.g., during step 512, and, as a result, determines a risk profile for the user, e.g., during step 514. The risk profile may indicate whether the user needs to improve at least one health attribute, e.g., potentially including the health attribute.

The mobile device determines, using the score for the health attribute and historical health data for the user, whether the score for the health attribute has changed since providing the instructions for presentation of the suggestion that describes how the user can improve a measure of the health attribute (516). For instance, the wearable device determines whether the task performed by the user improved the attribute score for the health attribute.

The mobile device may determine whether a score for a particular attribute or an overall score has improved over a period of time. For example, the mobile device may determine whether the score has improved over the past week, two weeks, month, or another appropriate period of time.

The mobile device provides instructions for presentation of data representing the score, the risk profile, and whether the score has changed (518). For instance, the wearable device presents a user interface indicating whether the score has changed. In some examples, the mobile device provides the instructions in response to determining that the score has changed by at least a threshold amount and does not provide the instructions otherwise. The mobile device may provide instructions for presentation of one, two or all three of the score, the risk profile, and an indication whether the score has changed.

The data representing the score may include a value for the score, an indication of whether the user can still improve the health attribute or another health attribute, or both. In some examples, the mobile device may determine that an attribute score for the health attribute satisfies a threshold attribute score, e.g., specific to the health attribute and not another health attribute, and that the user can improve a second health attribute. The mobile device may include information about the second health attribute in the data representing the score, e.g., information indicating that the user can improve the second health attribute.

The order of steps in the process 500 described above is illustrative only, and the generation of the risk score can be performed in different orders. For example, the mobile device may receive data from the sensors prior to, and after, providing the recommendation. The mobile device may use the initial data received from the sensors to determine an initial score for the health attribute, an overall score, or both. The mobile device may use the second data received from sensors to determine whether the initial score, the overall score, or both, have changed.

In some implementations, the process 500 can include additional steps, fewer steps, or some of the steps can be divided into multiple steps. For example, the mobile device may perform steps 506 through 518, steps 506 through 510 and step 518, steps 502 and 506 through 510, or any other appropriate combination of steps.

In some implementations, one or more of the steps may be performed by a server, e.g., the analysis system 402 from the environment 400. For example, the analysis system may generate an initial overall score for a user and provide the initial overall score to the mobile device with a task recommendation.

The mobile device presents the task recommendation to the user and monitors user attribute data for the user. The mobile device uses the monitored user attribute data to determine an updated overall score for the user. The mobile device may use the updated overall score to determine a risk profile. The mobile device may present information about the updated overall score, the risk profile, a change in the overall score, e.g., between the initial overall score and the updated overall score, or a combination of two or more of these.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML, page, to a user device, e.g., for purposes of displaying data to and receiving user input from a user interacting with the user device, which acts as a client. Data generated at the user device, e.g., a result of the user interaction, can be received from the user device at the server.

Figure 6:
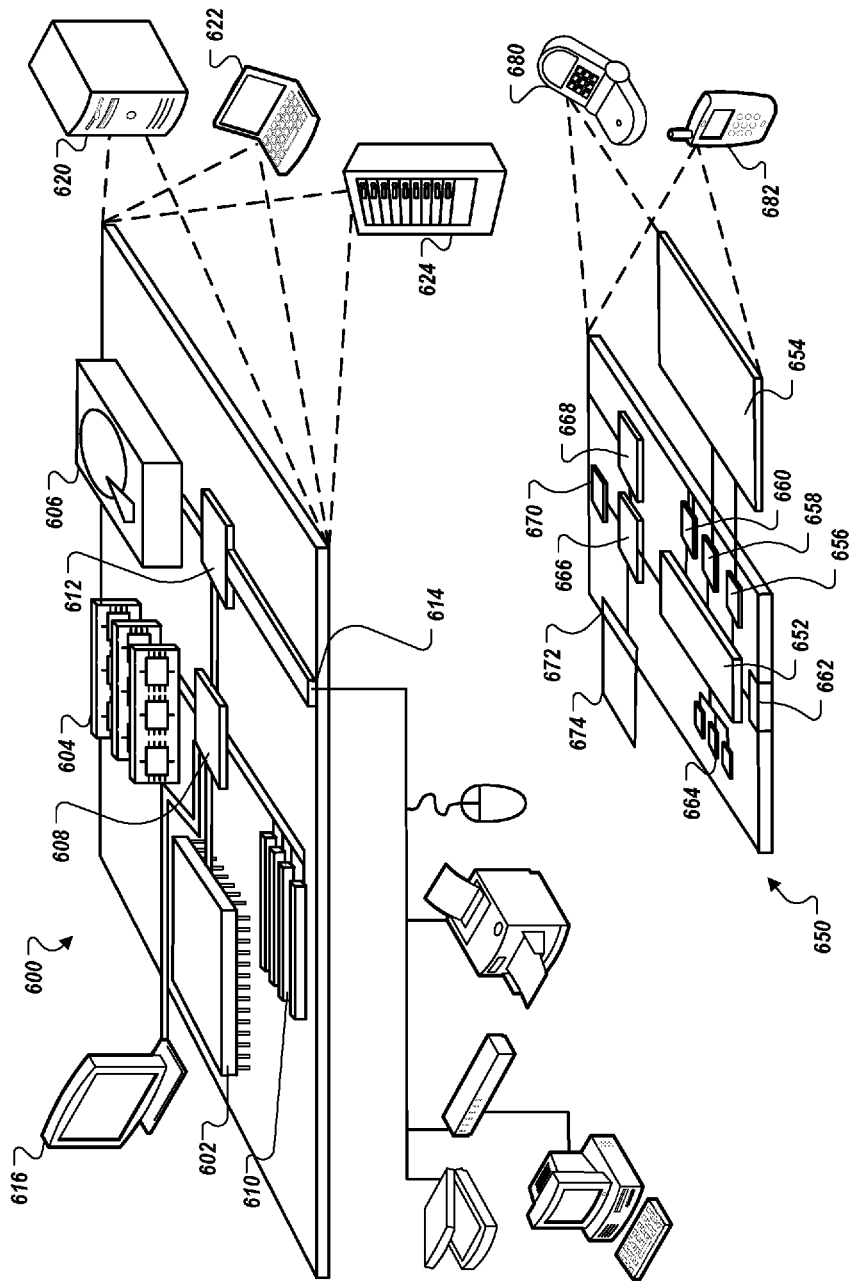
FIG. 6 is a block diagram of a computing system that can be used in connection with computer-implemented methods described in this document.

FIG. 6 is a block diagram of computing devices 600, 650 that may be used to implement the systems and methods described in this document, as either a client or as a server or plurality of servers. Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smartphones, smartwatches, head-worn devices, and other similar computing devices. The components shown here, their connections and relationships, and their functions, are meant to be exemplary only, and are not meant to limit implementations described and/or claimed in this document.

Computing device 600 includes a processor 602, memory 604, a storage device 606, a high-speed interface 608 connecting to memory 604 and high-speed expansion ports 610, and a low speed interface 612 connecting to low speed bus 614 and storage device 606. Each of the components 602, 604, 606, 608, 610, and 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as display 616 coupled to high speed interface 608. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 604 stores information within the computing device 600. In one implementation, the memory 604 is a computer-readable medium. In one implementation, the memory 604 is a volatile memory unit or units. In another implementation, the memory 604 is a non-volatile memory unit or units.

The storage device 606 is capable of providing mass storage for the computing device 600. In one implementation, the storage device 606 is a computer-readable medium. In various different implementations, the storage device 606 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 604, the storage device 606, or memory on processor 602.

The high speed controller 608 manages bandwidth-intensive operations for the computing device 600, while the low speed controller 612 manages lower bandwidth-intensive operations. Such allocation of duties is exemplary only. In one implementation, the high-speed controller 608 is coupled to memory 604, display 616 (e.g., through a graphics processor or accelerator), and to high-speed expansion ports 610, which may accept various expansion cards (not shown). In the implementation, low-speed controller 612 is coupled to storage device 606 and low-speed expansion port 614. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. It may also be implemented as part of a rack server system 624. In addition, it may be implemented in a personal computer such as a laptop computer 622. Alternatively, components from computing device 600 may be combined with other components in a mobile device (not shown), such as device 650. Each of such devices may contain one or more of computing device 600, 650, and an entire system may be made up of multiple computing devices 600, 650 communicating with each other.

Computing device 650 includes a processor 652, memory 664, an input/output device such as a display 654, a communication interface 666, and a transceiver 668, among other components. The device 650 may also be provided with a storage device, such as a microdrive or other device, to provide additional storage. Each of the components 650, 652, 664, 654, 666, and 668, are interconnected using various buses, and several of the components may be mounted on a common motherboard or in other manners as appropriate.

The processor 652 can process instructions for execution within the computing device 650, including instructions stored in the memory 664. The processor may also include separate analog and digital processors. The processor may provide, for example, for coordination of the other components of the device 650, such as control of user interfaces, applications run by device 650, and wireless communication by device 650.

Processor 652 may communicate with a user through control interface 658 and display interface 656 coupled to a display 654. The display 654 may be, for example, a TFT LCD display or an OLED display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may be provide in communication with processor 652, so as to enable near area communication of device 650 with other devices. External interface 662 may provide, for example, for wired communication (e.g., via a docking procedure) or for wireless communication (e.g., via Bluetooth or other such technologies).

The memory 664 stores information within the computing device 650. In one implementation, the memory 664 is a computer-readable medium. In one implementation, the memory 664 is a volatile memory unit or units. In another implementation, the memory 664 is a non-volatile memory unit or units. Expansion memory 674 may also be provided and connected to device 650 through expansion interface 672, which may include, for example, a SIMM card interface. Such expansion memory 674 may provide extra storage space for device 650, or may also store applications or other information for device 650. Specifically, expansion memory 674 may include instructions to carry out or supplement the processes described above, and may include secure information also. Thus, for example, expansion memory 674 may be provide as a security module for device 650, and may be programmed with instructions that permit secure use of device 650. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, or memory on processor 652.

Device 650 may communicate wirelessly through communication interface 666, which may include digital signal processing circuitry where necessary. Communication interface 666 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 668. In addition, short-range communication may occur, such as using a Bluetooth, WiFi, or other such transceiver (not shown). In addition, GPS receiver module 670 may provide additional wireless data to device 650, which may be used as appropriate by applications running on device 650.

Device 650 may also communicate audibly using audio codec 660, which may receive spoken information from a user and convert it to usable digital information. Audio codec 660 may likewise generate audible sound for a user, such as through a speaker, e.g., in a handset of device 650. Such sound may include sound from voice telephone calls, may include recorded sound (e.g., voice messages, music files, etc.) and may also include sound generated by applications operating on device 650.

The computing device 650 may be implemented in a number of different forms, as shown in the figure. For example, it may be implemented as a cellular telephone 680. It may also be implemented as part of a smartphone 682, personal digital assistant, or other similar mobile device.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A wearable device comprising:
   one or more sensors each of which monitor a user health attribute;
   a data processing apparatus; and
   a non-transitory computer readable storage medium in connected with the data processing apparatus and storing instructions executable by the data processing apparatus and upon such execution cause the data processing apparatus to perform operations comprising:
   providing instructions for presentation of a suggestion that describes how a user can improve a measure of a health attribute;
   determining a likelihood that a physical location of the wearable device is near a physical location with at least a threshold amount of vehicle traffic;
   determining whether the likelihood is greater than a threshold likelihood;
   determining whether audio content is being presented to the user; and
   lowering a volume of the audio content in response to (i) determining that the likelihood is greater than the threshold likelihood and (ii) determining that audio content is being presented to the user;
   receiving, from at least one of the sensors, health data for the user after providing the instructions for presentation of the suggestion that describes how the user can improve a measure of the health attribute;
   determining, using the health data, a score for the health attribute, wherein the score indicates a degree to which user performance of a task associated with the health attribute will improve the score;
   determining, using the score for the health attribute and historical health data for the user, whether the score for the health attribute has changed since providing the instructions for presentation of the suggestion that describes how the user can improve a measure of the health attribute; and providing instructions for presentation of data representing the score and whether the score has changed in response to determining, using the score for the health attribute and historical health data for the user, that the score for the health attribute has changed since providing the instructions for presentation of the suggestion that describes how the user can improve a measure of the health attribute.

2. The wearable device of claim 1, the operations comprising:
providing data that indicates instructions for presentation of information about two or more health attributes each of which the user can improve; and
receiving user input that specifies selection of a particular health attribute from the two or more health attributes in response to providing data that indicates instructions for presentation of information about two or more health attributes each of which the user can improve, wherein providing the data that indicates the instructions for presentation of the suggestion that describes how the user can improve a measure of a health attribute comprises providing data that indicates instructions for presentation of a suggestion that describes how the user can improve a measure of the particular health attribute in response to receiving the user input that indicates the selection of one of the two or more health attributes.

3. The wearable device of claim 1, wherein the at least one of the sensors:
monitors a measure of the health attribute of the user; and
provides data representing the measure of the health attribute to the data processing apparatus, wherein receiving, from the at least one of the sensors, the health data for the user comprises receiving, from the at least one of the sensors, the measure of the health attribute of the user.

4. The wearable device of claim 3, the operations comprising:
determining that the measure of the health attribute of the user does not correspond to historical patterns for the health attribute, wherein providing the instructions for presentation of the suggestion that describes how the user can improve the measure of a health attribute is responsive to determining that the measure of the health attribute of the user does not correspond to the historical patterns for the health attribute.

5. The wearable device of claim 1, the operations comprising:
determining, for each of two or more health attributes including the health attribute, a second score that indicates a degree to which user performance of a task associated with the corresponding health attribute will improve the second score; and
selecting, from the two or more health attributes, the health attribute with a highest second score from the second scores or a lowest second score from the second scores, wherein providing the instructions for presentation of the suggestion that describes how the user can improve a measure of the health attribute comprises providing the instructions for presentation of the suggestion that describes how the user can improve a measure of the selected health attribute with the highest second score from the second scores or the lowest second score from the second scores.

6. The wearable device of claim 1, wherein:
determining, using the health data, the score for the health attribute comprises determining the score for the health attribute using the health data for the user and a term for the health attribute in an equation used to determine an overall wellness score for the user;
the score indicates a degree to which user performance of a task associated with the health attribute will improve the overall wellness score; and
the overall wellness score indicates a degree to which user performance of a task associated with one of two or more health attributes will improve the overall wellness score, the at least one of the two or more health attributes including the health attribute.

7. The wearable device of claim 6, the operation comprising:
retrieving data representing the equation from a memory, wherein:
a training system generated at least part of the equation by fitting a model represented by the equation to historical health data for other users;
the equation includes one term for each of the two or more health attributes; and
determining, using the health data, the score for the health attribute comprises determining, using a term for the health attribute and the health data, the score for the health attribute.

8. The wearable device of claim 7, wherein a system generates at least part of the equation using empirical data.

9. The wearable device of claim 1, wherein providing the instructions for presentation of the suggestion that describes how the user can improve a measure of a health attribute comprises providing instructions for visual presentation of the suggestion that describes how the user can improve a measure of a health attribute.

10. The wearable device of claim 1, the operations comprising:
determining a physical location of the wearable device; and
determining, using the physical location of the wearable device, the suggestion that describes how the user can improve a measure of a health attribute.

11. The wearable device of claim 1, the operations comprising:
determining a predicted future physical location of the wearable device using future calendar data for the user; and
determining, using the predicted future physical location of the wearable device, the suggestion that describes how the user can improve a measure of a health attribute.

12. The wearable device of claim 1, the operations comprising:
determining current weather conditions or predicted weather conditions for a physical area at which the wearable device will be located; and
determining, using the current weather conditions or the predicted weather conditions, the suggestion that describes how the user can improve a measure of a health attribute.

13. A computer-implemented method comprising:
determining a predicted future physical location of a wearable device using future calendar data for a user of the wearable device;
determining, using the predicted future physical location of the wearable device, a suggestion that describes how the user can improve a measure of a health attribute;
providing instructions for presentation on a display of the suggestion that describes how the user can improve a measure of a health attribute;

receiving, from a sensor included in the wearable device that monitors a user health attribute, health data for the user;

determining, using the health data, a score for the health attribute, wherein the score indicates a degree to which user performance of a task associated with the health attribute will improve the score;

determining, using the score for the health attribute and historical health data for the user, whether the score for the health attribute has changed since providing the instructions for presentation of the suggestion that describes how the user can improve a measure of the health attribute; and providing instructions for presentation on a display of data representing the score and whether the score has changed.

14. A non-transitory computer readable storage medium storing instructions executable by a data processing apparatus and upon such execution cause the data processing apparatus to perform operations comprising:

providing instructions for presentation of a suggestion that describes how a user can improve a measure of a health attribute;

determining a likelihood that a physical location of a wearable device is near a physical location with at least a threshold amount of vehicle traffic;

determining whether the likelihood is greater than a threshold likelihood;

determining whether audio content is being presented to the user; and lowering a volume of the audio content in response to (i) determining that the likelihood is greater than the threshold likelihood and (ii) determining that audio content is being presented to the user;

receiving, from a sensor included in the wearable device that monitors a user health attribute, health data for the user after providing the instructions for presentation of the suggestion that describes how the user can improve a measure of the health attribute;

determining, using the health data, a score for the health attribute, wherein the score indicates a degree to which user performance of a task associated with the health attribute will improve the score;

determining, using the score for the health attribute and historical health data for the user, whether the score for the health attribute has changed since providing the instructions for presentation of the suggestion that describes how the user can improve a measure of the health attribute; and providing instructions for presentation of data representing the score and whether the score has changed in response to determining, using the score for the health attribute and historical health data for the user, that the score for the health attribute has changed since providing the instructions for presentation of the suggestion that describes how the user can improve a measure of the health attribute.

15. The computer readable storage medium of claim 14, the operations comprising:

providing data that indicates instructions for presentation of information about two or more health attributes each of which the user can improve; and receiving user input that specifies selection of a particular health attribute from the two or more health attributes, wherein providing the data that indicates the instructions for presentation of the suggestion that describes how the user can improve a measure of a health attribute comprises providing data that indicates instructions for presentation of a suggestion that describes how the user can improve a measure of the particular health attribute in response to receiving the user input that indicates the selection of one of the two or more health attributes.

16. The computer readable storage medium of claim 14, wherein receiving, from the sensor that monitors the user health attribute, the health data for the user comprises receiving, from a sensor that monitors a measure of the health attribute of the user, a measure of the health attribute of the user.

17. The computer readable storage medium of claim 16, the operations comprising:

determining that the measure of the health attribute of the user does not correspond to historical patterns for the health attribute, wherein providing the instructions for presentation of the suggestion that describes how the user can improve the measure of a health attribute is responsive to determining that the measure of the health attribute of the user does not correspond to the historical patterns for the health attribute.

18. The computer readable storage medium of claim 14, the operations comprising:

determining, for each of two or more health attributes including the health attribute, a second score that indicates a degree to which user performance of a task associated with the corresponding health attribute will improve the second score; and selecting, from the two or more health attributes, the health attribute with a highest second score from the second scores or a lowest second score from the second scores, wherein providing the instructions for presentation of the suggestion that describes how the user can improve a measure of the health attribute comprises providing the instructions for presentation of the suggestion that describes how the user can improve a measure of the selected health attribute with the highest second score from the second scores or the lowest second score from the second scores.

19. The wearable device of claim 1, comprising:

a speaker, wherein:

determining whether audio content is being presented to the user comprises determining whether the speaker is presenting the audio content; and lowering the volume of the audio content comprises lowering the volume of the audio content presented by the speaker.

20. The wearable device of claim 1, wherein:

determining whether audio content is being presented to the user comprises determining whether another device, connected to the wearable device, is presenting the audio content; and lowering the volume of the audio content comprises sending instructions to the other device to cause the other device to lower the volume of the audio content.

21. The wearable device of claim 20, wherein determining whether another device, connected to the wearable device, is presenting the audio content comprises determining whether a smart phone, connected to the wearable device, is presenting the audio content.

* * * * *